(12) United States Patent
Möckel et al.

(10) Patent No.: US 6,713,289 B2
(45) Date of Patent: Mar. 30, 2004

(54) NUCLEOTIDE SEQUENCES WHICH CODE FOR THE ENO GENE

(75) Inventors: Bettina Möckel, Bielefeld (DE); Walter Pfefferle, Halle (DE); Thomas Hermann, Bielefeld (DE); Alfred Pühler, Bielefeld (DE); Jörn Kalinowski, Bielefeld (DE); Brigitte Bathe, Salzkotten (DE)

(73) Assignee: Degussa AG, Dusseldorf (DE)

( * ) Notice: Subject to any disclaimer, the term of this patent is extended or adjusted under 35 U.S.C. 154(b) by 0 days.

(21) Appl. No.: 09/860,768

(22) Filed: May 21, 2001

(65) Prior Publication Data

US 2002/0082403 A1 Jun. 27, 2002

Related U.S. Application Data

(63) Continuation-in-part of application No. 09/455,779, filed on Dec. 7, 1999, now abandoned.

(30) Foreign Application Priority Data

Oct. 5, 1999 (DE) .......................................... 199 47 791

(51) Int. Cl.[7] .......................... C12N 15/64; C12N 9/00; C12N 1/20; C12N 15/00; C12N 15/01; C12P 13/04; C12P 13/08; C07H 21/04

(52) U.S. Cl. .......................... 435/115; 435/41; 435/106; 435/183; 435/252.3; 435/320.1; 435/440; 435/442; 435/447; 435/471; 536/23.2; 536/23.7

(58) Field of Search ............................ 435/252.3, 320.1, 435/41, 106, 115, 183, 440, 442, 471; 536/23.2, 23.7

(56) References Cited

FOREIGN PATENT DOCUMENTS

| EP | 0 197 335 A | 10/1996 |
|---|---|---|
| WO | 01 00844 A | 1/2001 |
| WO | 01 02543 A | 1/2001 |
| WO | 01 04322 A | 1/2001 |
| WO | 01 04325 A | 1/2001 |

OTHER PUBLICATIONS

Hermann Thomas et al: "Mapping and identification of Corynebacterium glutamicum proteins by two–dimensional gel electrophoresis and microsequencing." ELECTROPHORESIS, Bd. 19, Nr. 18 Dec. 1998; p. 3217–3221, XP000979523.

Database EMBL accession: Z92539, Mar. 3, 1997, Cole S T et al: "Mycobacterium tuberculosis H37Rv complete genome; segment 47/162" XP002160101.

Database EMBL accession: P96377, Jul. 15, 1998, Cole S T et al: Encolase (EC 4.2.1.11) (2–phosphoglycerate dehydratase) (2–phospho–D–Glycerate Hydro–Lyase). XP002160102.

Eikmanns Bernhard J: "Identification, sequence analysis, and expression of a Corynebacterium glutamicum gene cluster encoding the three glycolytic enzymes glyceraldehyde–3–phosphate dehydrogenase, 3–phosphoglycerate kinase, and triosephosphate isomerase." Journal of Bacteriology, Bd. 174, Nr. 19, 1992, p. 6076–6086, XP000979491.

*Primary Examiner*—Manjunath Rao
(74) *Attorney, Agent, or Firm*—Pillsbury Winthrop LLP (57) ABSTRACT

The present invention is directed to nucleotide sequences coding for a bacterial enolase enzyme. These sequences may be used in improved methods for the fermentative preparation of amino acids using coryneform bacteria.

15 Claims, 2 Drawing Sheets

NUCLEOTIDE SEQUENCES WHICH CODE FOR THE ENO GENE

This is a continuation-in-part of application Ser. No. 09/455,779 filed Dec. 7, 1999 now abandoned.

FIELD OF THE INVENTION

The present invention provides nucleotide sequences coding for a bacterial enolase enzyme. It encompasses processes for the fermentative preparation of amino acids using coryneform bacteria in which the eno gene is amplified.

BACKGROUND OF THE INVENTION

L-amino acids, especially L-lysine, are used in the feeding of animals, in human medicine and in the pharmaceutical industry. They are typically produced by fermenting strains of coryneform bacteria, especially *Corynebacterium glutamicum*. Because of the great importance of amino acids, work is continually being done to improve production processes. Improvements may concern measures relating to the fermentation process (e.g., relating to stirring and oxygen supply) or the composition of the nutrient medium, (e.g., relating to the sugar concentration during the fermentation). They may also concern the purification of product (e.g., by ion-exchange chromatography) or the intrinsic performance properties of the microorganism itself.

To improve the performance properties of amino acid-producing microorganisms, methods of mutagenesis, selection and mutant selection are often employed. These methods may be used to obtain strains that are resistant to antimetabolites, such as, for example, the lysine analogue S-(2-aminoethyl)-cysteine, or which are auxotrophic for amino acids which are important in terms of regulation, and produce L-amino acids. In addition, methods of recombinant DNA technology have been used to improve the L-amino-acid-producing strains of *Corynebacterium glutamicum* by amplifying individual genes of amino acid biosynthesis. General articles on this subject include Kinoshita ("Glutamic Acid Bacteria," in: *Biology of Industrial Microorganisms*, Demain and Solomon (eds.), Benjamin Cummings, London, UK, 1985, 115–142; Hilliger, *BioTec* 2:40–44 (1991); Eggeling, *Amino Acids* 6:261–272 (1994); Jetten, et al, *Crit. Rev. Biotech.* 15:73–103 (1995); and Sahm, et al., *Ann. New York Acad. Sci.* 782:25–39 (1996)).

SUMMARY OF THE INVENTION

The present invention is based upon the isolation of a bacterial gene coding for the enolase enzyme and the discovery that amino acid synthesis in coryneform bacteria is increased when the activity of this enzyme is enhanced. Bacteria may be treated in a number of different ways to enhance enolase activity but, most typically enhancement will result from bacteria being transformed with an expression vector encoding the enzyme. "Enhanced" refers to an increase in enolase activity in the treated bacteria relative to the amount of activity in untreated bacteria.

In its first aspect, the present invention is directed to an isolated polynucleotide from coryneform bacteria containing a polynucleotide sequence coding for the eno gene. The polynucleotide is selected from the group consisting of: a) a polynucleotide that is at least 70% identical with a polynucleotide that codes for a polypeptide containing the amino-acid sequence of SEQ ID NO:2; and b) a polynucleotide that codes for a polypeptide containing an amino acid sequence that is at least 70% identical (and preferably 80 or 90% identical) with the amino-acid sequence of SEQ ID NO:2. In either case, the polypeptide must exhibit the activity of the enolase enzyme and, prefereably, it is a recombinant DNA replicative in coryneform bacteria.

The term "isolated" means separated out of its natural environment. Thus, a protein or polypeptide that has been purified would be isolated for the purposes of the present invention. "Polynucleotide" in refers to polyribonucleotides and, preferably, polydeoxyribonucleotides, it being possible for these to be non-modified or modified RNA or DNA. "Polypeptides" is understood as meaning peptides or proteins which comprise two or more amino acids bonded via peptide bonds.

A preferred polynucleotide coding for the enolase enzyme is that having the nucleotide sequence of SEQ ID NO:1. The invention includes not only polynucleotides having this specific sequence but also those that are at least 70% homologous (and preferably 80 or 90% homologous) to SEQ ID NO:1 and and in which one or more of the codons are replaced with a degenerate codon or in which there is a neutral sense mutation that does not alter the activity of the enolase enzyme. In addition, the invention encompasses a corynebacteria containing the any of the polynucleotides that are a part of the present invention.

Polynucleotide sequences derived from SEQ ID NO:1 may be used as hybridization probes for RNA, cDNA and DNA, in order to isolate the full length cDNA which coding for enolase and to isolate genes which have a high degree of homology with the enolase gene. Such oligonucleotides serving as probes or primers (e.g. for PCR) should be at least 15, and preferably at least 30 to 50 base pairs in length.

The inventors have found that improved activity occurs when the L-glutamic acid at position 223 of SEQ ID NO:2 is replaced by another proteinogenic amino acid. Thus, the invention includes enolase proteins with include this mutation and polypeptides which code for the mutated polypeptides. In a preferred embodiment, the L-glutamic acid at positon 223 is replaced with L-lysine as shown in SEQ ID NO:4. One way to code for a polypeptide to code for this is shown herein as SEQ ID NO:3 which is similar to SEQ ID NO:1 but with an adenine at position 817.

In another aspect, the invention is directed to a method for the production an L-amino acid, by: a) fermenting a coryneform bacteria that produces the amino acid and in which the activity of the enolase enzyme is enhanced; and b) isolating the L-amino acid from either the bacteria or from the medium used to grow the bacteria. Preferably, the amino acid being produced by the method is L-lysine and the enhancement of enolase activity results from the overexpression of the eno gene. The term "overexpression" as used in this instance refers to an increase in the amount of mRNA transcribed relative to the amount of transcription occurring in untreated bacteria. The coryneform bacteria may be transformed with a nucleotide sequence coding for the enolase enzyme of SEQ ID NO:2 or in which the L-glutamic acid at position 223 of SEQ ID NO:2 is replaced by another proteinogenic L-amino acid, preferably L-lysine.

In addition to exhibiting enhanced enolase activity, the bacteria used to produce amino acids may have undergone additional genetic alterations to increase production. For example, the bacteria may be engineered to over-express one more genes encoding enzymes used in the biosynthetic pathway of of said L-amino acid or metabolic paths that reduce the formation of of the amino acid, e.g. L-lysine, may be at least partially eliminated. Specific genes that may be overexpressed to increase amino acid synthesis include:

dapA gene coding for dihydrodipicolinate synthase; the lysC gene coding for a feedback-resistant aspartate kinase; the gap gene coding for glyceraldehyde-3-phosphate dehydrogenase; the tpi gene coding for triosephosphate isomerase; the pgk gene coding for 3-phosphoglycerate kinase; and the pyc gene coding for pyruvate carboxylase.

BRIEF DESCRIPTION OF THE FIGURES

FIG. 1.

FIG. 2.

DETAILED DESCRIPTION OF THE INVENTION

The present invention is based upon the development of improved methods for the production of L-amino acids, especially L-lysine, by fermentation. Unless otherwise indicated, any mention of L-lysine or lysine herein is to be understood as meaning not only the base but also salt forms of the amino acid, such as, for example, lysine monohydrochloride or lysine sulfate. This also applies with respect to other amino acids.

The invention provides a process for the production of L-amino acids, especially L-lysine, by fermentation using coryneform bacteria which, especially, already produce the desired amino acid and in which the activity of the enzyme malate: quinone oxidoreductase (mqo) is enhanced, especially by over-expression of its gene. The term "enhanced" or "enhancement" in this connection describes a change which leads to an increase in the intracellular activity of the enzyme relative to the activity seen in the unaltered microorganism. For example, enhancement may be accomplished by increasing the copy number of the gene, using a strong promoter, or using a gene or allele that codes for a corresponding enzyme having a high degree of activity, and optionally combining those measures. "Amplification" refers to a specific procedure for achieving an enhancement whereby the number of DNA molecules carrying a gene or genes, an allele or alleles, a regulatory signal or signals or any other genetic feature is increased.

The microorganisms provided by the present invention can produce L-amino acids, especially L-lysine, from glucose, saccharose, lactose, fructose, maltose, molasses, starch, cellulose or from glycerol and ethanol. They are representatives of coryneform bacteria, especially of the genus Corynebacterium. In this genus, a preferred species is *Corynebacterium glutamicum*. Examples of suitable strains of bacteria are as follows:

| | | |
|---|---|---|
| Corynebacterium glutamicum | | ATCC13032 |
| Corynebacterium acetoglutamicum | | ATCC15806 |
| Corynebacterium acetoacidophilum | | ATCC13870 |
| Corynebacterium thermoaminogenes | FERM | BP-1539 |
| Brevibacterium flavum | | ATCC14067 |
| Brevibacterium lactofermentum | | ATCC13869 |
| Brevibacterium divaricatum | | ATCC14020. |

Examples of suitable L-amino-acid-producing, especially L-lysine-producing, mutants and strains produced therefrom, include:

| | | |
|---|---|---|
| Corynebacterium glutamicum | FERM-P | 1709 |
| Brevibacterium flavum | FERM-P | 1708 |
| Brevibacterium lactofermentum | FERM-P | 1712 |
| Corynebacterium glutamicum | FERM-P | 6463 |
| Corynebacterium glutamicum | FERM-P | 6464 |
| Corynebacterium glutamicum | DSM | 5715 |

Gene isolation may be accomplished by constructing a gene library of this microorganism in *E. coli*. Procedures for making such libraries are well known in the art (see, e.g., Winnacker: *Gene und Klone Eine Einführung in die Gentechnologie*, Verlag Chemie, Weinheim, Germany, 1990; Sambrook et al., *Molecular Cloning, A Laboratory Manual*, Cold Spring Harbor Laboratory Press, 1989); Kohara, et al., *Cell* 50:495–508 (1987)). Bathe et al. (*Mol. Gen. Genet.* 252:255–265 (1996)) describe a gene library of *C. glutamicum* ATCC13032 which was constructed with the aid of the cosmid vector SuperCos I (Wahl et al., *Proc. Nat'l Acad. Sci. USA* 84:2160–2164 (1987)) in the *E. coli* K-12 strain NM554 (Raleigh et al., *Nuc. Acids Res.* 16:1563–1575 (1988)). A gene library of *C. glutamicum* ATCC13032 was also made by Börmann et al. (*Mol. Microbiol.* 6(3): 317–326)) using the cosmid pHC79 (Hohn et al, *Gene* 11:291–298 (1980)). A gene library of *C. glutamicum* may also be prepared in *E. coli* using plasmids such as pBR322 (Bolivar, *Life Sci.* 25:807–818 (1979)) or pUC9 (Viera et al., *Gene* 19:259–268 (1982)). Suitable hosts are, in particular, those *E. coli* strains that are restriction- and recombination-defective, e.g., strain DH5αmcr (Grant et al., *Proc. Nat'l Acad. Sci. USA* 87:4645–4649 (1990)). DNA fragments can be subcloned and sequenced in vectors that are suitable for sequencing, such as those described by Sanger et al. (*Proc. Natl Acad. Sci. USA* 74:5463–5467, (1977)). Using these methods, the inventors isolated the eno gene of *C. glutamicum*. This codes for the enzyme enolase (EC 4.2.1.11) and was determined to have the sequence shown herein as SEQ ID NO:1. The amino acid sequence of the corresponding protein was derived from the DNA sequence and is shown herein as SEQ ID NO:2.

Coding DNA sequences which correspond to SEQ ID NO:1 by the degeneracy of the genetic code are part of the invention. Conservative amino acid exchanges, such as the exchange of glycine for alanine or aspartic acid for glutamic acid, are known among experts as "sense mutations" and do not usually lead to a substantial change in the activity of the protein, i.e., they are of neutral function. Similarly, it is known that changes in the N and/or C terminus of proteins typically do not substantially impair, and can even stabilize, their function (see, e.g., Ben-Bassat, et al., *J. Bacteriol.* 169:751–757 (1987); O'Regan, et al., *Gene* 77:237–251 (1989); Sahin-Toth, et al., *Prot. Sci.* 3:240–247 (1994); and Hochuli et al., *Bio/Tech.* 6:1321–1325 (1988)). Amino acid sequences which are differ from SEQ ID NO:2 only with respect to differences of this type which do not substantially affect enolase activity are also part of the invention.

DNA sequences which hybridize with SEQ ID NO:1 or parts of SEQ ID NO:1 are a included within the scope of the invention, as are DNA sequences which are prepared by the polymerase chain reaction (PCR) using primers derived from SEQ ID NO:1. Such oligonucleotides typically have a length of at least 15 base pairs. Instructions for identifying DNA sequences by means of hybridization can be found, inter alia, in the handbook "The DIG System Users Guide for Filter Hybridization" (Boehringer Mannheim GmbH, Mannheim, Germany, (1993)) and in Liebl et al. (*Int. J. Sys. Bacteriol.* 41:255–260 (1991)). A description of methods for amplifying DNA sequences using the polymerase chain reaction (PCR) can be found, inter alia, in a handbook by Gait (*Oligonukleotide synthesis: a practical approach*, IRL Press, Oxford, UK (1984)) and by Newton et al (*PCR*, Spektrum Akademischer Verlag, Heidelberg, Germany (1994)).

The inventors have found that coryneform bacteria produce amino acids, in particular L-lysine, in an improved manner after over-expression of the eno gene. In order to achieve over-expression, the copy number of the eno gene can be increased, or the promoter and regulation region, which is located in front of the structural gene, can be mutated. Expression cassettes, which are inserted in front of the structural gene, have the same effect. By means of inducible promoters it is additionally possible to increase the expression in the course of the production of L-lysine by fermentation. Expression is likewise improved by measures for lengthening the life of the m-RNA, e.g., by inhibiting the rate at which enzyme is degraded. The genes or gene constructs can either be present in plasmids with different copy numbers or be integrated and amplified in the chromosome.

Alternatively, over-expression of the eno gene can be achieved by changing the composition of the bacterial growth medium and the manner in which culturing is carried out. The person skilled in the art will find a detailed description of procedures that can be followed for carrying out these objectives in a number of publications, including: Martin et al., *Bio/Technology* 5:137–146 (1987); Guerrero, et al., *Gene* 138:35–41 (1994); Tsuchiya, et al., *Bio/Technology* 6:428–430 (1988); Eikmanns, et al., *Gene* 102:93–98 (1991); EP-B 0 472 869; U.S. Pat. No. 4,601,893; Schwarzer, et al., *Bio/Technology* 9:84–87 (1991); Reinscheid, et al., *AppL. Environment. Microbiol.* 60:126–132 (1994); LaBarre, et al., *J. BacterioL* 175:1001–1007 (1993); WO 96/15246; Malumbres, et al., *Gene* 134:15–24 (1993); Jensen et al., *Biotech. Bioeng.* 58:191–195 (1998); Makrides, *Microbiol. Rev.* 60:512–538 (1996) and in other standard textbooks of genetics and molecular biology.

By way of example, the eno gene according to the invention was over-expressed with the aid of plasmids. Suitable plasmids are those which are replicated in coryneform bacteria. Suitable plasmid vectors such as pZ1 (Menkel et al., *App. Envir. Microbiol.* 64:549–554 (1989)), pEKEx1 (Eikmanns et al., *Gene* 102:93–98 (1991)) and pHS2-1 (Sonnen et al., *Gene* 107:69–74 (1991)) are based on the the cryptic plasmids pHM1519, pBL1 and pGA1. Other plasmid vectors such as those based on pCG4 (U.S. Pat. No. 4,489,160), pNG2 (Serwold-Davis, et al., FEMS Microbiol. Lett. 66:119–124 (1990)) and pAG1 (U.S. Pat. No. 5,158,891) can also be used.

In addition, it was found that the replacement of the amino acid L-glutamic acid at position 223 of the enolase enzyme (see SEQ ID NO:2) by any other proteinogenic amino acid, especially L-lysine (see SEQ ID No. 4), results in an enhancement of amino acid synthesis. Thus, coryneform bacteria that carry an enolase enzyme having such an amino acid replacement produce amino acids, especially L-lysine, in an improved manner. In a preferred embodiment, the replacement of L-glutamic acid by L-lysine is accomplished by the substitution of guanine at position 817 of the eno gene by adenine, as shown in the nucleotide sequence of SEQ ID NO:3.

Mutation of the eno gene can be carried out using classic methods and employing mutagenic substances such as, e.g., N-methyl-N'-nitro-N-nitrosoquanidine or ultraviolet light. Mutagenesis can also be performed using in vitro methods such as those involving treatment with hydroxyl amine (Konickova-Radochova, *Folia Microbiol.* 13(3): 226–230, Prague (1968)), mutagenic oligonucleotides (Brown, *Gentechnologie für Einsteiger*, Spektrum Akademischer Verlag, Heidelberg, (1993)) and the polymerase chain reaction (PCR) (Newton, et al., *PCR*, Spektrum Adademischer Verlag, Heidelberg (1994)).

After sequencing, the eno alleles or genes may be introduced into a suitable host. Replicating plasmid vectors can be used for this. It is likewise possible to insert the eno allele or gene into the chromosome of a suitable host by gene replacement as described, for example, by Schwarzer and P ühler (*Bio/Tech.* 9:84–87 (1991)). The allele or gene in question is cloned into a vector that is not replicative for *C. glutamicum* and this vector is subsequently transferred via transformation or conjugation into the desired host. Insertion takes place by homologous recombination involving a first crossover event bringing about integration and a second crossover event in the target sequence bringing about excision. This method was used by Peters-Wendisch et al. (*Microbiol.* 144:915–927 (1998)) to replace the pyc gene of *C. glutamicum* with a pyc allele carrying a deletion.

In addition, the method of chromosomal gene amplification can be used (see, e.g., Reinscheid et al., *App. Environ. Microbiol* 60:126–132 (1994)). In this method, the complete gene or allele is cloned into a plasmid vector that can replicate in a host (typically *E. coli*) but not in *C. glutamicum*. Potential vectors include: pSUP301 (Simon et al., *Bio/Tech.* 1:784–791 (1983)); pK18mob or pK19mob (Schäfer et al., *Gene* 145:69–73 (1994)); pGEM-T (Promega Corp., Madison, Wis., USA); pCR2.1-TOPO (Schuman, J Biol. Chem. 269:32678-84 (1994); U.S. Pat. No. 5,487,993); pCR®Blunt (Invitrogen Co., Gronigen, The Netherlands; Bernard et al., *J Mol. Biol.* 234:534–541 (1993)); pEM1 (Schrumpf et al., *J. Bacteriol.* 173:4510–4516 (1991)); and pBGS8 (Spratt et al., *Gene* 41:337–342 (1986)). The plasmid vector containing the gene or allele to be amplified is subsequently transferred by conjugation or transformation into the desired strain of *C. glutamicum*. Methods for carrying out conjugation and transformation have been described by, inter alia: Schäfer et al. (*App. Environ. Microbiol.* 60:756–759 (1994)); Thierbach et al. (*App. Microbiol. Biotech.* 29:356–362 (1988)); Dunican, et al., (*Bio/Tech.* 7:1067–1070 (1989)); and Tauch, et al. (*FEMS Microbiol Lett.* 123:343–347 (1994)). After homologous recombination by means of a crossover event, the resulting strain contains at least two copies of the particular gene or allele.

Accordingly, further subject matter of the invention is constituted by coryneform bacteria that contain the enolase enzyme proteins in which the amino acid sequence shown under SEQ ID NO:2 at position 223 is replaced by another amino acid with the exception of L-glutamic acid. A further aspect of this invention is constituted by coryneform bacteria that contain a corresponding enzyme protein in which the amino acid L-glutamic acid at position 223 of the enzyme protein (see, SEQ ID NO:2) is replaced by L-lysine (see, SEQ ID N: 4).

In addition to the eno gene, it can be advantageous for the production of amino acids, especially L-lysine, to over-express one or more enzymes involved in their biosynthetic pathway, in glycolysis, in the anaplerotic metabolic pathway, in the citric-acid cycle or in amino acid export. Thus, for the production of L-lysine it may be advantageous to over-express both eno and one or more of the following:

the dapA gene coding for dihydrodipicolinate synthase (EP-B 0 197 335);

the lysC gene coding for a feedback-resistant aspartokinase (EP-B 0387527, U.S. Pat. No. 5,688,671);

the gap gene coding for glyceraldehyde-3-phosphate dehydrogenase (Eikmanns, *J Bacteriol.* 174:6076–6086 (1992));

the tpi gene coding for triosephosphate isomerase (Eikmanns, *J Bacteriol.* 174:6076–6086 (1992));

the pgk gene coding for 3-phosphoglycerate kinase (Eikmanns, *J Bacteriol.* 174:6076–6086 (1992));

the pyc gene coding for pyruvate carboxylase (Eikmanns, *J Bacteriol.* 174:6076–6086 (1992)); and the lysE gene coding for the lysine export protein (DE-A-195 48 222).

In addition to over-expressing the eno gene, it may also be advantageous for the production of amino acids, in particular L-lysine, to eliminate undesirable side reactions (Nakayama: "Breeding of Amino Acid Producing Microorganisms", in: *Overproduction of Microbial Products*, Krumphanzl, Sikyta, Vanek (eds.), Academic Press, London, UK, 1982)).

The microorganisms produced according to the invention may be cultivated continuously or discontinuously in a batch process, in a fed batch, or by a repeated fed batch process for the purpose of producing L-amino acids. A summary of cultivation methods is described in the textbook by Chmiel (*Bioprozesstechnik 1. Einführung in die Bioverfahrenstechnik*, Gustav Fischer, Verlag, Stuttgart, (1991)) or in the textbook by Storhas (*Bioreaktoren und periphere Einrichtungen*, Vieweg Verlag, Braunschweig/Wiesbaden (1994)). The culture medium to be used must meet the requirements of the strain being used for production. Descriptions of culture media for various microorganisms are contained in the handbook *Manual of Methods for General Bacteriology* of the American Society for Bacteriology, Washington D. C., USA, (1981).

Examples of compounds that can be used as a carbon source include: sugars and carbohydrates such as glucose, saccharose, lactose, fructose, maltose, molasses; starch and cellulose; oils and fats such as soybean oil, sunflower oil, groundnut oil and coconut fat; fatty acids, such as palmitic acid, stearic acid and linoleic acid; alcohols such as glycerol and ethanol; and organic acids such as acetic acid. These substances may be used individually or in the form of a mixture. Examples of compounds that can be used as a nitrogen source include: organic nitrogen-containing compounds such as peptones, yeast extract, meat extract, malt extract, corn steep liquor, soybean flour and urea; or inorganic compounds such as ammonium sulfate, ammonium chloride, ammonium phosphate, ammonium carbonate and ammonium nitrate. The nitrogen sources may be used individually or in the form of a mixture.

Compounds that can be use as a phosphorus source include potassium dihydrogen phosphate and dipotassium hydrogen phosphate or the corresponding sodium-containing salts. The culture medium must also contain salts of metals, such as, for example, magnesium sulfate or iron sulfate, which are necessary for growth. Finally, essential growth substances such as amino acids and vitamins may be used in addition to the above-mentioned substances. Moreover, suitable pre-stages may be added to the culture medium. The mentioned substances may be added to the culture in the form of a single batch or may be fed in a suitable manner during the cultivation.

In order to control the pH of the culture, basic compounds, such as sodium hydroxide, potassium hydroxide, ammonia, or acid compounds, such as phosphoric acid or sulfuric acid, can be used. For controlling the development of foam, antifoams, such as, for example, fatty acid polyglycol esters, may be added.

Plasmid stability can be maintained by adding substances having a selective action, for example antibiotics, to the medium. In order to maintain aerobic conditions, oxygen or oxygen-containing gas mixtures, such as, for example, air, are introduced into the culture.

The temperature of the culture is normally from 20° C. to 45° C. and preferably from 25° C. to 40° C. Culturing is continued until a maximum of the desired L-amino acid has formed. That aim is normally achieved within a period of from 10 hours to 160 hours. Analysis of L-amino acids may be carried out by anion-exchange chromatography with subsequent ninhydrin derivatization, as described by Spackman et al. (*Analyt. Chem.* 30:1190 (1958)).

The invention may be further understood by reference to the following non-limiting examples.

EXAMPLES

Example 1

Production of a Genomic Cosmid Gene Bank from Corynebacterium Glutamicum ATCC 13032

Chromosomal DNA from *Corynebacterium glutamicum* ATCC 13032 was isolated as described in Tauch et al., (*Plasmid* 33:168–179 (1995)) and partially cleaved with the restriction enzyme Sau3AI (Amersham Pharmacia, Freiburg, Germany, product description Sau3AI, code No. 27-0913-02). The DNA fragments were dephosphorylated with shrimp alkaline phosphatase (Roche Molecular Biochemicals, Mannheim, Germany, product description SAP, code No. 1758250). The DNA of the cosmid vector SuperCos1 (Wahl et al. *Proc. Nat'l Acad. Sci. USA* 84:2160–2164 (1987)) obtained from the Stratagene company (La Jolla, USA, product description SuperCos1 cosmid Vektor Kit, Code No. 251301) was cleaved with the restriction enzyme XbaI (Amersham Pharmacia, Freiburg, Germany, product description XbaI, code No. 27-0948-02) and also dephosphorylated with shrimp alkaline phosphatase. The cosmid DNA was subsequently cleaved with the restriction enzyme BamHI (Amersham Pharmacia, Freiburg, Germany, product description BamHI, code No. 27-0868-04). The cosmid DNA treated in this manner was mixed with the treated ATCC13032 DNA and the batch treated with T4 DNA ligase (Amersham Pharmacia, Freiburg, Germany, product description T4 DNA ligase, code No. 27-0870-04).

The ligation mixture was subsequently packed in phages with the aid of Gigapack II XL packing extracts (Stratagene, La Jolla, USA, product description Gigapack II XL packing extract code No. 200217). For the infection of the *E. coli* strain NM554 (Raleigh et al., *NucL. Ac. Res.* 16:1563–1575 (1988)), the cells were taken up in 10 mM $MgSO_4$ and mixed with an aliquot of the phage suspension. The infection and titering of the cosmid library were carried out as described by Sambrook, et al. (*Molecular Cloning: A Laboratory Manual*, Cold Spring Harbor, 1989), the cells being plated out on LB agar (Lennox, *Virology* 1:190 (1955)) with 100 µg/ml ampicillin. After incubation overnight at 37° C., recombinant individual clones were selected.

Example 2

Isolation and Sequencing of the Eno Gene

The cosmid DNA of an individual colony was isolated with the Qiaprep Spin Miniprep Kit (Product No. 27106, Qiagen, Hilden, Germany) in accordance with the manufacturer's instructions and partly cleaved with the restriction enzyme Sau3AI (Amersham Pharmacia, Freiburg, Germany, Product Description Sau3AI, Product No. 27-0913-02). The DNA fragments were dephosphorylated with shrimp alkaline phosphatase (Roche Molecular Biochemicals, Mannheim, Germany, Product Description SAP, Product No. 1758250). After separation by gel electrophoresis, cosmid fragments in the size range of 1500 to 2000 bp were isolated with the QiaExII Gel Extraction Kit (Product No. 20021, Qiagen, Hilden, Germany). The DNA of the sequencing vector pZero-1, obtained from the company Invitrogen (Groningen, The Netherlands, Product Description Zero Background Cloning Kit, Product No. K2500-01) was cleaved with the restriction enzyme BamHI (Amersham Pharmacia, Freiburg, Germany, Product Description BamHI, Product No. 27-0868-04). The ligation of the cosmid fragments in the sequencing vector pZero-1 was carried out as described by Sambrook, et al. (*Molecular Cloning: A laboratory Manual*, Cold Spring Harbor, 1989), the DNA mixture being incubated overnight with T4 ligase (Pharmacia Biotech, Freiburg, Germany). This ligation mixture was subsequently electroporated into the *E. coli* strain DH5αMCR (Grant, *Proc. Natl. Acad. Sci.* USA 87:4645–4649 (1990); Tauch, et al., *FEMS Microbiol. Lett.* 123:343-7 (1994)) and plated out onto LB agar (Lennox, *Virology* 1:190 (1955)) with 50 µg/ml zeocine. The plasmid preparation of the recombinant clones took place using the Biorobot 9600 (Product No. 900200, Qiagen, Hilden, Germany). Sequencing took place according to the dideoxy chain termination method of Sanger, et al. (*Proc. Natl. Acad. Sci.* U.S.A. 74:5463–5467 (1977)) with modifications according to Zimmermann et al. (*Nucl. Ac. Res.* 18:1067 (1990)). The "RR dRhodamin Terminator Cycle Sequencing Kit" of PE Applied Biosystems (product No. 403044, Weiterstadt, Germany) was used. The gel electrophoretic separation and analysis of the sequencing reaction took place in a "Rotiphorese NF Acrylamid/Bisacrylamid" gel (29:1) (product No. A124.1, Roth, Karlsruhe, Germany) with the "ABI Prism 377" sequencing device of PE Applied Biosystems (Weiterstadt, Germany).

The raw sequence data obtained was subsequently processed using the Staden program packet (*Nucl. Ac. Res.* 14:217–231 (1986)) version 97-0. The individual sequences of the pZero1 derivatives were assembled to a cohesive contig. The computer-supported coding range analysis was prepared with the program XNIP (Staden, *NucL Ac. Res.* 14:217–231 (1986)). Further analyses were carried out with the "BLAST search programs" (Altschul et al., *Nucl. Ac. Res.* 25:3389–3402 (1997)) against the non-redundant databank of the "National Center for Biotechnology Information" (NCBI, Bethesda, Md., USA).

The nucleotide sequence obtained is shown as SEQ ID NO:1. An analysis of the nucleotide sequence yielded an open reading frame of 1275 base pairs that was designated as the "eno gene." The gene codes for a protein of 425 amino acids.

Example 3

Production of Shuttle Vector pXT-enoex for Enhancing the Eno Gene in *C. Glutamicum*

3.1. Cloning of the eno gene

Chromosomal DNA was isolated from the strain ATCC 13032 according to the method of Eikmanns et al. (*Microbiology* 140:1817–1828 (1994)). Based on the sequence of the eno gene known from Example 2, the following oligonucleotides were selected for the polymerase chain reaction:

eno-exl (SEQ ID NO:5):

5' TTG GCA TAG GAG GCC ACA GT 3' eno-ex2 (SEQ ID NO:6):

5' ATT TAG CCC TGA AAG CGT GG 3'.

The primers shown were synthesized by the ARK Scientific GmbH Biosystems company (Darmstadt, Germany) and the PCR reaction was carried out according to the standard PCR method of Innis, et al (*PCR Protocols. A Guide to Methods and Applications*, Academic Press, 1990) with Pwo polymerase of the Roche Diagnostics GmbH company (Mannheim, Germany). The primers make possible, with the aid of the polymerase chain reaction, the amplification of a DNA fragment approximately 1.3 kb large that carries the eno gene. The DNA sequence of the amplified DNA fragment was tested by sequencing.

3.2. Production of the *E. coli—C. Glutamicum* Shuttle Vector pEC-XT99A

The *E. coli* expression vector pTRAC99A (Amman et al., *Gene* 69:301 315 (1988)) was used as starting vector for the construction of the *E. coli—C. glutamicum* shuttle expression vector pEC-ST99A. After BspHI restriction cleavage (Diagnostics GmbH, Mannheim, Germany, product description BspHI, product No. 1467123) and subsequent Klenow treatment (Amersham Pharmacia Biotech, Freiburg, Germany, product description Klenow Fragment of DNA Polymerase I, product No. 27-0928-01; method according to Sambrook, et al, *Molecular Cloning: A Laboratory Manual*, Cold Spring Harbor, 1989), the ampicillin resistance gene (bla) was replaced by the tetracycline resistance gene of the *C. glutamicum* plasmid pAG1 (GenBank Accession No. AF121000). To this end the resistance-gene-carrying construct was cloned as an AluI fragment (Amersham Pharmacia Biotech, Freiburg, Germany, product description AluI, product No. 27-0884-01) into the linearized *E. coli* expression vector pTRC99A. The ligation was carried out as described by Sambrook et al., 1989, *Molecular Cloning: A Laboratory Manual*, Cold Spring Harbor) and the DNA mixture incubated overnight with T4 ligase (Amersham Pharmacia Biotech, Freiburg, Germany, product description T4-DNA ligase, product No. 27-0870-04). This ligation mixture was subsequently electroporated into the *E. coli* strain DH5αmcr (Grant, *Proc. Natl. Acad. Sci.* USA 87:4645–4649 (1990); Tauch, et al, *FEMS Microbiol. Lett.* 123:343-7 (1994)). The constructed *E. coli* expression vector was designated with pXT99A.

The plasmid pGA1 (Sonnen et al., *Gene*, 107:69–74 (1991)) was used as the basis for cloning a minimal replicon from *Corynebacterium glutamicum*. A fragment 3484 bp in size was cloned into the vector pK18mob2 (Tauch et al., *Arch. Microbiol.* 169:303–312 (1998)) fragmented with SmaI and PstI (Amersham Pharmacia Biotech, Freiburg, Germany, product description SmaI, product No. 27-0942-02) by means of BalI/PstI restriction cleavage (Promega GmbH, Mannheim, Germany, product description BalI, product No. R6691; Amersham Pharmacia Biotech, Freiburg, Germany, product description, PstI, product No. 27-0976-01) of vector pGA1. A fragment 839 bp in size was deleted by means of BamHI/XhoI restriction cleavage (Amersham Pharmacia Biotech, Freiburg, Germany, product description BamHI, product No. 27-086803, product description XhoI, product No. 27-0950-01) and subsequent Klenow treatment (Amersham Pharmacia Biotech, Freiburg, Germany, product description Klenow fragment of DNA polymerase I, product No. 27-0928-01; method according to Sambrook et al., *Molecular Cloning: A Laboratory Manual*, Cold Spring Harbor, 1989). The *C. glutamicum* minimal replicon was cloned as 2645 bp fragment into the *E. coli* expression vector pXT99A from the construct religated with T4 ligase (Amersham Pharmacia Biotech, Freiburg, Germany, product description T4-DNA ligase, product No. 27-0870-04). To this end the DNA of the construct carrying the minimal replicon was cleaved with the restriction enzymes KpnI (Amersham Pharmacia Biotech, Freiburg, Germany, product description KpnI, product No. 27-0908-01) and PstI (Amersham Pharmacia Biotech, Freiburg, Germany, product description PstI, product No. 27-0886-03) and a 3'–5'-exonuclease treatment (Sambrook et al., *Molecular Cloning: A Laboratory Manual*, Cold Spring Harbor, 1989) was subsequently carried out by means of Klenow polymerase (Amersham Pharmacia Biotech, Freiburg, Germany, product description Klenow fragment of DNA polymerase I, product No. 27-0928-01).

In a parallel batch, the *E. coli* expression vector pXT99A was cleaved with the restriction enzyme RsrII (Roche Diagnostics, Mannheim, Germany, product description RsrII, product No. 1292587) and prepared for ligation with Klenow polymerase (Amersham Pharmacia Biotech, Freiburg, Germany, Klenow fragment of DNA polymerase I, product No. 27-0928-01). The ligation of the minimal replicon with vector construct pXT99A was carried out as described by Sambrook et al., (*Molecular Cloning: A Laboratory Manual*, Cold Spring Harbor, 1989) during which the DNA mixture was incubated overnight with T4 ligase (Amersham Pharmacia Biotech, Freiburg, Germany, product description T4-DNA ligase, product No. 27-0870-04).

The *E. coli C. glutamicum* shuttle expression vector pEC-XT99A constructed as described above was transferred by electroporation (Liebl, et al., *FEMS Microbiol. Lett.* 53:299–303 (1989)) into *C. glutamicum* DSM5715. The selection of the transformants took place on LBHIS agar consisting of 18.5 g/l brain-heart infusion bullion, 0.5 M sorbitol, 5 g/l bacto-trypton, 2.5 g/l bacto-yeast extract, 5 g/l NaCl and 18 g/l bacto agar that had been supplemented with 5 mg/l tetracycline. The incubation was carried out 2 days at 33° C.

Figure 1:
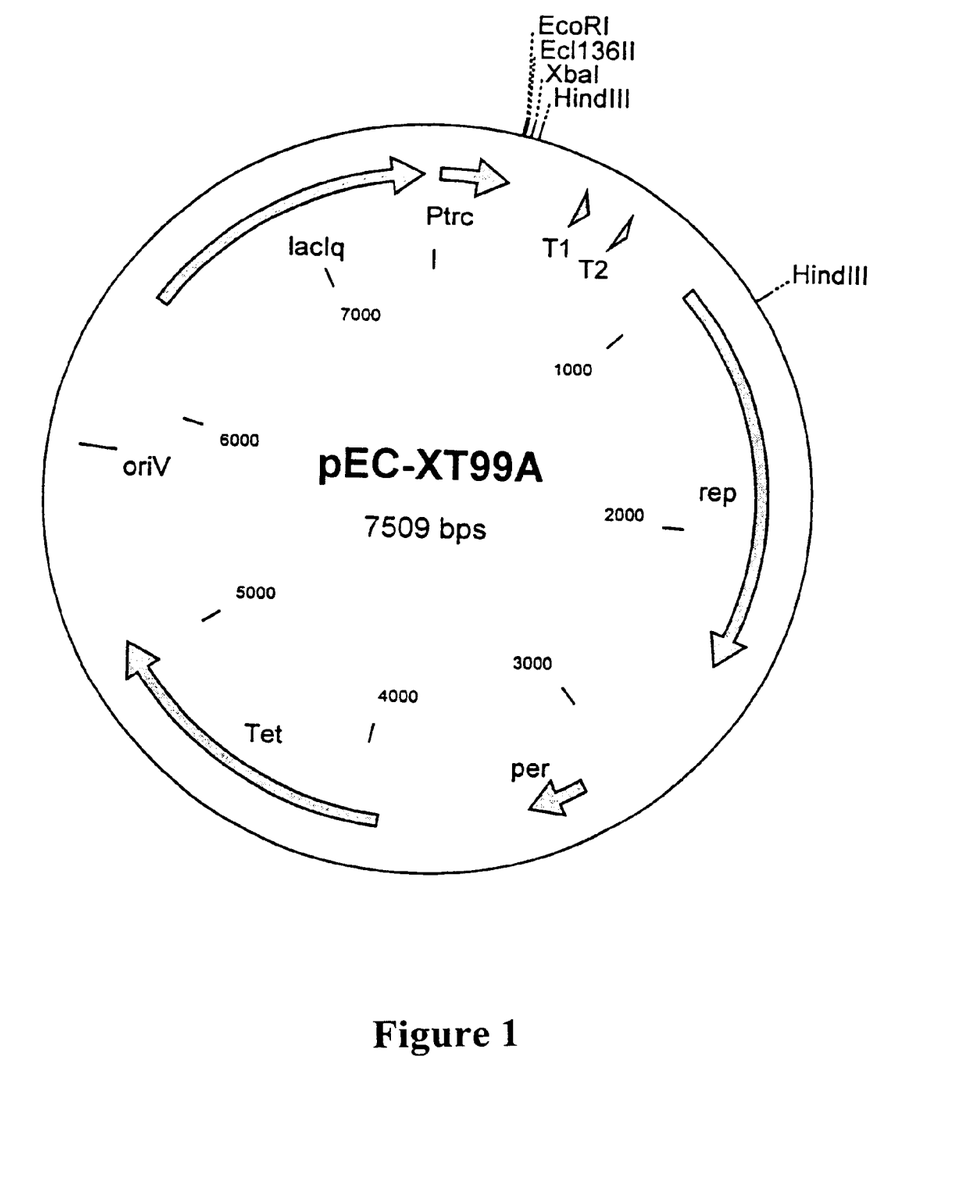
FIG. 1 is a map of plasmid pEC-XT99A.

Plasmid DNA was isolated from a transformant according to the customary methods (Peters-Wendisch, et al., *Microbiol.* 144:915–926 (1998)), cut with restriction endonuclease HindIII and the plasmid checked by subsequent agarose gel electrophoresis. The plasmid construct obtained in this manner was designated pEC-XT99A and is shown in FIG. 1. The strain obtained by electroporation of plasmid pEC-XT99A into *Corynebacterium glutamicum* strain DSM5715 was named DSM5715pEC-XT99A and deposited as DSM 12967 in the German Collection for Microorganisms and Cell Cultures (DSMZ, Braunschweig, Germany) according to the Treaty of Budapest.

3.3. Cloning of eno in the *E. coli—C. glutamicum* Shuttle Vector pEC-XT99A

The *E. coli —C. glutamicum* shuttle vector pEC-XT99a described in example 3.2 was used as vector. DNA of this plasmid was completely cleaved with restriction enzyme Ecl136II and subsequently dephosphorylated with shrimp alkaline phosphatase (Roche Diagnostics GmbH, Mannheim, Germany, product description SAP, product No. 1758250).

Figure 2:
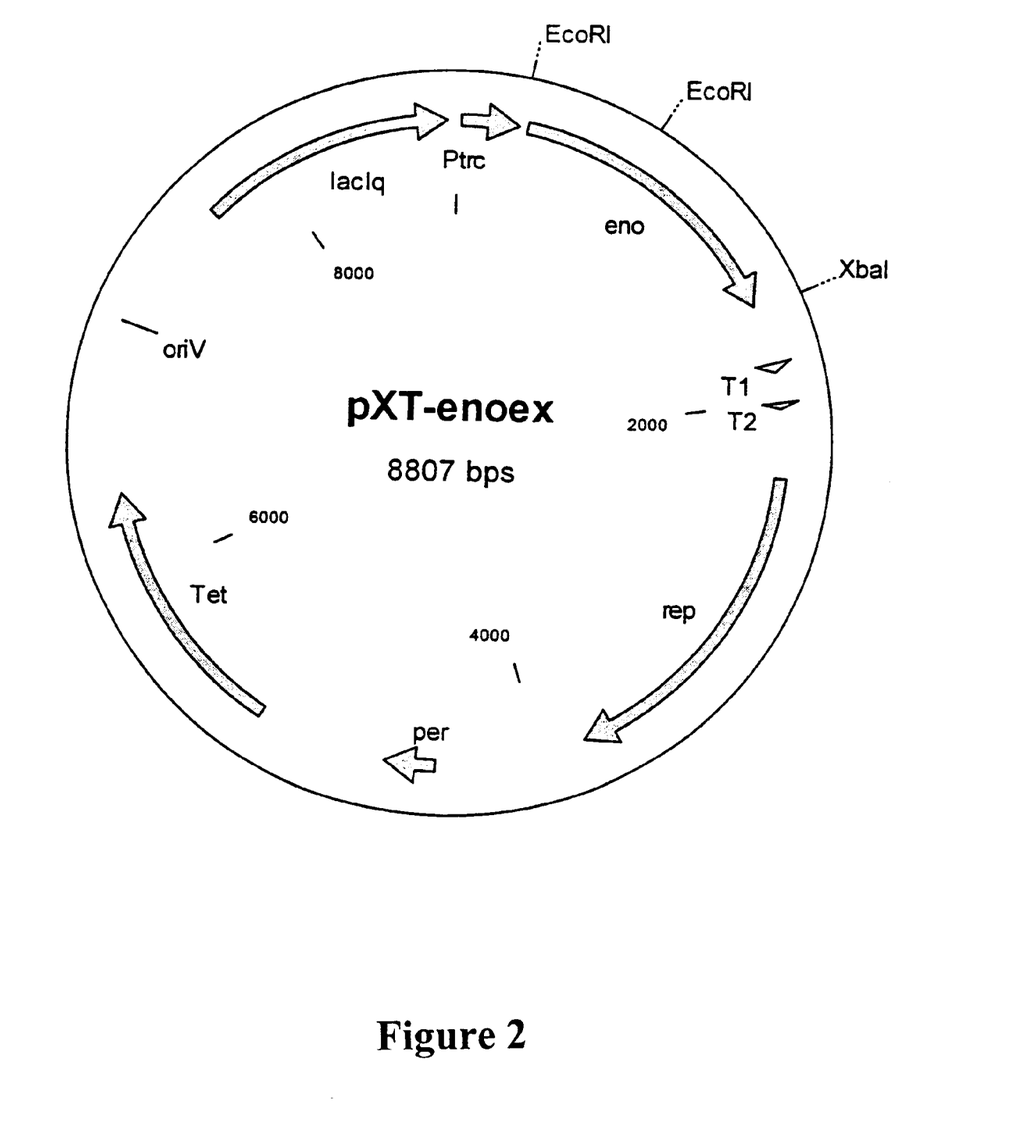
FIG. 2 is a map of plasmid pXT-enoex.

The eno fragment obtained as described in example 3.1 was mixed with the prepared vector pEC-XT99A and the batch treated with T4-DNA ligase (Amersham Pharmacia Biotech, Freiburg, Germany, product description T4-DNA ligase, Code No. 27-0870-04). The ligation batch was transformed into the *E. coli* strain DH5αmcr (Grant, *Proc. Natl. Acad. Sci. USA,* 87:4645–4649 (1990)). The selection of plasmid-carrying cells took place by plating the transformation batch out onto LB agar with 5 mg/l tetracycline. After incubation overnight at 37° C., recombinant individual clones were selected. Plasmid DNA was isolated from a transformant with the Qiaprep Spin Miniprep Kit (Product No. 27106, Qiagen, Hilden, Germany) according to the instructions of the manufacturer and cleaved with the restriction enzymes EcoRI and XbaI in order to check the plasmid by subsequent agarose gel electrophoresis. The plasmid obtained was named pXT-enoex and is shown in FIG. 2.

Example 4

Transformation of the Strain DSM5715 with the Plasmid pXT-enoex

The strain DSM5715 was transformed with the plasmid pXT-enox using the electroporation method described by Liebl et al., (*FEMS Microbiol. Lett.* 53:299–303 (1989)). The selection of the transformants took place on LBHIS agar consisting of 18.5 g/l brain-heart infusion bullion, 0.5 M sorbitol, 5 g/l bacto-tryptone, 2.5 g/l bacto-yeast extract, 5 g/l NaCl and 18 g/l bacto-agar that had been supplemented with 5 mg/l tetracycline. The incubation took place for 2 days at 33° C.

Plasmid DNA was isolated from a transformant according to standard methods (Peters-Wendisch et al., *Microbiol.* 144:915–927 (1998)), cut with the restriction endonucleases EcoRI and XbaI and the plasmid checked by subsequent agarose gel electrophoresis. The strain obtained was named DSM5715/pXT-enoex.

Example 5

Production of Lysine

The *C. glutamicum* strain DSM5715/pXT-enoex obtained in Example 4 was cultivated in a nutrient medium suitable for the production of lysine and the lysine content determined in the culture residue. To this end, the strain was first incubated on an agar plate with the appropriate antibiotic (brain-heart agar with tetracycline (5 mg/l)) for 24 hours at 33° C. Starting with this agar-plate culture, a preculture was inoculated (10 ml medium in a 100 ml Erlenmeyer flask). The full medium CgIII was used as medium for the preculture.

| Medium Cg III | |
|---|---|
| NaCl | 2.5 g/l |
| Bactopeptone | 10 g/l |
| Bacto-yeast extract | 10 g/l |
| Glucose (autoclaved separately) | 2% (w/w) |
| The pH was adjusted to pH 7.4. | |

Tetracycline ((5 mg/l) was added to this mixture. The preculture was incubated for 16 hours at 33° C. at 240 rpm on an agitator. A main culture was inoculated from this preculture so that the initial OD (660 nm) of the main culture was 0.05. Medium MM was used for the main culture.

| Medium MM | |
|---|---|
| CSL (corn steep liquor) | 5 g/l |
| MOPS (morpholinopropane sulfonic acid) | 20 g/l |
| Glucose (autoclaved separately) | 100 g/l |
| $(NH_4)_2SO_4$ | 25 g/l |
| $KH_2PO_4$ | 0.1 g/l |
| $MgSO_4 * 7 H_2O$ | 1.0 g/l |
| $CaCl_2 * 2 H_2O$ | 10 mg/l |
| $FeSO_4 * 7 H_2O$ | 10 mg/l |
| $MnSO_4 * H_2O$ | 5.0 mg/l |
| Biotin (sterilized by filtration) | 0.3 mg/l |
| Thiamine * HCl (sterilized by filtration) | 0.2 mg/l |
| L-leucine (sterilized by filtration) | 0.1 g/l |
| $CaCO_3$ | 25 g/l |

CSL, MOPS and the saline solution were adjusted with ammonia water to pH 7 and autoclaved. The sterile substrate- and vitamin solutions were then added along with the $CaCo_3$, that had been autoclaved dry. The cultivation took place in 10 ml volume in a 100 ml Erlenmeyer flask with flow spoilers. Tetracycline (5 mg/l) was added. Incubation was performed at 33° C. and 80% air humidity. After 72 hours, the OD was determined at a measuring wavelength of 660 nm with a Biomek 1000 (Beckmann Instruments GmbH, Munich). The lysine amount formed was determined with an amino-acid analyzer of the Eppendorf-BioTronik company (Hamburg, Germany) by ion-exchange chromatography and postcolumn derivatization with ninhydrin detection. Table 1 shows the result of the test.

TABLE 1

| Strain | OD (660) | Lysine-HCl g/l |
|---|---|---|
| DSM5715/pEC-XT99A | 7.4 | 15.5 |
| DSM5715/pXT-enox | 7.5 | 16.5 |

| | |
|---|---|
| per: | Gene for monitoring the copy number from pGA1 |
| oriV: | ColE1-like origin from pMB1 |
| rep: | Plasmid-coded replication origin from *C. glutamicum* plasmid pGA1 |
| Ptrc: | trc promoter from pTRC99A |
| T1, T2: | Terminator regions 1 and 2 from pTRC99A |
| lacIq: | repressor gene of the Lac operon |
| Tet: | Resistance gene for tetracycline |
| eno: | Enolase gene eno from *C. glutamicum* |
| EcoRI: | Cleavage site of restriction enzyme HindIII |
| XbaI: | Cleavage site of restriction enzyme XbaI |

What is claimed is:

1. A method for production of L-lysine amino acid, comprising:
   a) fermenting a coryneform bacterium that produces said L-lysine amino acid, wherein said coryneform bacterium transformed with a vector comprising an isolated polynucleotide, wherein said isolated polynucleotide is selected from the group consisting of an isolated polynucleotide encoding an enolase enzyme comprising the amino acid sequence of SEQ ID NO:2 or an isolated polynucleotide encoding enolase enzyme comprising the amino acid sequence of SEQ ID NO:2 wherein the glutamic acid at position 223 is replaced with another proteinogenic Lysine acid; and
   b) isolating said Lysine amino acid from said coryneform bacteria or from the medium used to grow said coryneform bacterium.

2. A method for production of L-lysine amino acid, comprising:
   a) fermenting an isolated coryneform bacterium that produces said L-lysine amino acid, wherein said isolated coryneform bacterium comprises a polynucleotide encoding an enolase enzyme comprising the amino acid sequence of SEQ ID NO:2, wherein the glutamic acid at position 223 is replaced by another proteinogenic Lysine amino acid, and
   b) isolating said Lysine amino acid from said coryneform bacteria or from the medium used to grow said coryneform bacterium.

3. The method of claim 1, wherein said isolated polynucleotide encoding an enolase enzyme comprises SEQ ID NO:1 or nucleotides 151 to 1425 of SEQ ID NO:1 wherein the nucleobase guanine at position 817 is replaced by adenine.

4. The method of claim 1, wherein said isolated polynucleotide encoding an enolase enzyme is comprised in a vector.

5. The method of claim 1 wherein said isolated polynucleotide encoding an enolase enzyme is transferred into the genome of said coryneform bacterium.

6. The method of claim 1 wherein the activity of said enolase enzyme encoded by said isolated polynucleotide is enhanced by overexpression.

7. The method of claim 2 wherein said polynucleotide encoding an enolase enzyme comprises SEQ ID NO:1 or nucleotides 151 to 1425 of SEQ ID NO:1 wherein the nucleobase guanine at position 817 is replaced by adenine.

8. The method of either of claim 1 or 2, wherein said coryneform bacterium comprises an overexpressed dapA gene of Corynebacterium glutamicum coding for dihydrodipicolinate synthase.

9. A method for preparing L-lysine amino acid, comprising:
   a) transforming a coryneform bacteria with a vector comprising;
      1) an isolated polynucleotide encoding enolase enzyme comprising the amino acid sequence of SEQ ID NO:2 or 2) an isolated polynucleotide encoding enolase enzyme comprising the amino acid sequence of SEQ ID NO:2, wherein the glutamic acid at position 232 is replaced with another proteinogenic L-lysine amino acid;

b) culturing said transformed coryneform bacteria under conditions suitable to enhance the activity of said enzyme by overexpression; and c) isolating the L-lysine amino acid produced.

10. The method of either of claim 1 or 2, wherein said coryneform bacterium comprises an overexpressed lysC gene of Corynebacterium glutamicum coding for a feed back resistant aspartate kinase.

11. The method of either of claim 1 or 2, wherein said coryneform bacterium comprises an overexpressed gap gene of *Corynebacterium glutamicum* coding for glyceraldehyde-3-phosphate dehydrogenase.

12. The method of either of claim 1 or 2, wherein said coryneform bacterium comprises an overexpressed tpi gene of *Corynebacterium glutamicum* coding for triosephosphate isomerase.

13. The method of either of claim 1 or 2, wherein said coryneform bacterium comprises an overexpressed pgk gene of *Corynebacterium glutamicum* coding for 3-phosphoglycerate kinase.

14. The method of either of claim 1 or 2, wherein said coryneform bacterium comprises an overexpressed pyc gene of *Corynebacterium glutamicum* coding for pyruvate carboxylase.

15. The method of either of claim 1 or 2, wherein said coryneform bacterium comprises an overexpressed lysE gene of *Corynebacterium glutamicum* coding for lysine export protein.

* * * * *

SEQUENCE LISTING

<160> NUMBER OF SEQ ID NOS: 6

<210> SEQ ID NO 1
<211> LENGTH: 1578
<212> TYPE: DNA
<213> ORGANISM: Corynebacterium glutamicum

<400> SEQUENCE: 1

```
ggctggggat atgggtagtt ttcgccacta atttcaactg attgcctcat cgaaacaaga      60
ttcgtgcaac aattgggtgt agacgtgatt gaagacattt gatcacgtga ataattctag     120
ttagctccca agttggcata ggaggccaca gtggctgaaa tcatgcacgt attcgctcgc     180
gaaattctcg actcccgcgg taacccaacc gtcgaggcag aggttttcct ggatgacggt     240
tcccacggtg tcgcaggtgt tccatccggc gcatccaccg gcgtccacga ggctcatgag     300
ctgcgtgacg gtggcgatcg ctacctgggc aagggcgttt tgaaggcagt tgaaaacgtc     360
aacgaagaaa tcggcgacga gctcgctggc ctagaggctg acgatcagcg cctcatcgac     420
gaagcaatga tcaagcttga tggcaccgcc aacaagtccc gcctgggtgc aaacgcaatc     480
cttggtgttt ccatggctgt tgcaaaggct gctgctgatt ccgcaggcct cccactgttc     540
cgctacatcg gtgaccaaa cgcacacgtt cttccagttc caatgatgaa catcatcaac     600
ggtggcgctc acgctgactc cggtgttgac gttcaggaat tcatgatcgc tccaatcggt     660
gcagagacct tctctgaggc tctccgcaac ggcgcggagg tctaccacgc actgaagtcc     720
gtcatcaagg aaaagggcct gtccaccgga cttggcgatg agggcggctt cgctccttcc     780
gtcggctcca cccgtgaggc tcttgacctt atcgttgagg caatcgagaa ggctggcttc     840 acccaggca aggacatcgc tcttgctctg gacgttgctt cctctgagtt cttcaaggac     900
ggcacctacc acttcgaagg tggccagcac tccgcagctg agatggcaaa cgtttacgct     960
```

-continued

```
gagctcgttg acgcgtaccc aatcgtctcc atcgaggacc cactgcagga agatgactgg    1020
gagggttaca ccaacctcac cgcaaccatc ggcgacaagg ttcagatcgt tggcgacgac    1080
ttcttcgtca ccaaccctga cgcctgaag gagggcatcg ctaagaaggc tgccaactcc    1140
atcctggtta aggtgaacca gatcggtacc ctcaccgaga ccttcgacgc tgtcgacatg    1200
gctcaccgcg caggctacac ctccatgatg tcccaccgtt ccggtgagac cgaggacacc    1260
accattgctg acctcgcagt tgcactcaac tgtggccaga tcaagactgg tgctccagca    1320
cgttccgacc gtgtcgcaaa gtacaaccag cttctccgca tcgagcagct gcttggcgac    1380
gccggcgtct acgcaggtcg cagcgcattc ccacgctttc agggctaaat aaaagcgctt    1440
ttcgacgccc ggtaacctca aggttgccgg gcgtcgttgc cttactactg ttactggtgt    1500
gactatgatc gaggattatg gcaaagcaga agaaaactca taaaggcctt gttcctgtct    1560
caagcaggga acgtgctt                                                  1578
```

<210> SEQ ID NO 2
<211> LENGTH: 425
<212> TYPE: PRT
<213> ORGANISM: Corynebacterium glutamicum

<400> SEQUENCE: 2

```
Val Ala Glu Ile Met His Val Phe Ala Arg Glu Ile Leu Asp Ser Arg
 1               5                  10                  15

Gly Asn Pro Thr Val Glu Ala Glu Val Phe Leu Asp Asp Gly Ser His
                20                  25                  30

Gly Val Ala Gly Val Pro Ser Gly Ala Ser Thr Gly Val His Glu Ala
            35                  40                  45

His Glu Leu Arg Asp Gly Gly Asp Arg Tyr Leu Gly Lys Gly Val Leu
        50                  55                  60

Lys Ala Val Glu Asn Val Asn Glu Glu Ile Gly Asp Glu Leu Ala Gly
 65                  70                  75                  80

Leu Glu Ala Asp Asp Gln Arg Leu Ile Asp Glu Ala Met Ile Lys Leu
                 85                  90                  95

Asp Gly Thr Ala Asn Lys Ser Arg Leu Gly Ala Asn Ala Ile Leu Gly
            100                 105                 110

Val Ser Met Ala Val Ala Lys Ala Ala Asp Ser Ala Gly Leu Pro
        115                 120                 125

Leu Phe Arg Tyr Ile Gly Gly Pro Asn Ala His Val Leu Pro Val Pro
    130                 135                 140

Met Met Asn Ile Ile Asn Gly Gly Ala His Ala Asp Ser Gly Val Asp
145                 150                 155                 160

Val Gln Glu Phe Met Ile Ala Pro Ile Gly Ala Glu Thr Phe Ser Glu
                165                 170                 175

Ala Leu Arg Asn Gly Ala Glu Val Tyr His Ala Leu Lys Ser Val Ile
            180                 185                 190

Lys Glu Lys Gly Leu Ser Thr Gly Leu Gly Asp Glu Gly Phe Ala
        195                 200                 205

Pro Ser Val Gly Ser Thr Arg Glu Ala Leu Asp Leu Ile Val Glu Ala
    210                 215                 220

Ile Glu Lys Ala Gly Phe Thr Pro Gly Lys Asp Ile Ala Leu Ala Leu
225                 230                 235                 240

Asp Val Ala Ser Ser Glu Phe Phe Lys Asp Gly Thr Tyr His Phe Glu
                245                 250                 255

Gly Gly Gln His Ser Ala Ala Glu Met Ala Asn Val Tyr Ala Glu Leu
```

```
                    260                 265                 270
Val Asp Ala Tyr Pro Ile Val Ser Ile Glu Asp Pro Leu Gln Glu Asp
                275                 280                 285
Asp Trp Glu Gly Tyr Thr Asn Leu Thr Ala Thr Ile Gly Asp Lys Val
            290                 295                 300
Gln Ile Val Gly Asp Asp Phe Phe Val Thr Asn Pro Glu Arg Leu Lys
305                 310                 315                 320
Glu Gly Ile Ala Lys Lys Ala Ala Asn Ser Ile Leu Val Lys Val Asn
                325                 330                 335
Gln Ile Gly Thr Leu Thr Glu Thr Phe Asp Ala Val Asp Met Ala His
            340                 345                 350
Arg Ala Gly Tyr Thr Ser Met Met Ser His Arg Ser Gly Glu Thr Glu
        355                 360                 365
Asp Thr Thr Ile Ala Asp Leu Ala Val Ala Leu Asn Cys Gly Gln Ile
    370                 375                 380
Lys Thr Gly Ala Pro Ala Arg Ser Asp Arg Val Ala Lys Tyr Asn Gln
385                 390                 395                 400
Leu Leu Arg Ile Glu Gln Leu Leu Gly Asp Ala Gly Val Tyr Ala Gly
                405                 410                 415
Arg Ser Ala Phe Pro Arg Phe Gln Gly
            420                 425

<210> SEQ ID NO 3
<211> LENGTH: 1578
<212> TYPE: DNA
<213> ORGANISM: Corynebacterium glutamicum

<400> SEQUENCE: 3
ggctggggat atgggtagtt ttcgccacta atttcaactg attgcctcat cgaaacaaga     60
ttcgtgcaac aattgggtgt agacgtgatt gaagacattt gatcacgtga ataattctag    120
ttagctccca agttggcata ggaggccaca gtggctgaaa tcatgcacgt attcgctcgc    180
gaaattctcg actcccgcgg taacccaacc gtcgaggcag aggttttcct ggatgacggt    240
tcccacggtg tcgcaggtgt tccatccggc gcatccaccg gcgtccacga ggctcatgag    300
ctgcgtgacg gtggcgatcg ctacctgggc aagggcgttt gaaggcagt tgaaaacgtc    360
aacgaagaaa tcggcgacga gctcgctggc ctagaggctg acgatcagcg cctcatcgac    420
gaagcaatga tcaagcttga tggcaccgcc aacaagtccc gcctgggtgc aaacgcaatc    480
cttggtgttt ccatggctgt tgcaaaggct gctgctgatt ccgcaggcct cccactgttc    540
cgctacatcg gtggaccaaa cgcacacgtt cttccagttc caatgatgaa catcatcaac    600
ggtggcgctc acgctgactc cggtgttgac gttcaggaat tcatgatcgc tccaatcggt    660
gcagagacct tctctgaggc tctccgcaac ggcgcggagg tctaccacgc actgaagtcc    720
gtcatcaagg aaaagggcct gtccaccgga cttggcgatg agggcggctt cgctccttcc    780
gtcggctcca cccgtgaggc tcttgacctt atcgttaagg caatcgagaa ggctggcttc    840
accccaggca aggacatcgc tcttgctctg gacgttgctt cctctgagtt cttcaaggac    900
ggcacctacc acttcgaagg tggccagcac tccgcagctg agatggcaaa cgtttacgct    960
gagctcgttg acgcgtaccc aatcgtctcc atcgaggacc cactgcagga agatgactgg   1020
gagggttaca ccaacctcac cgcaaccatc ggcgacaagg ttcagatcgt tggcgacgac   1080
ttcttcgtca ccaaccctga gcgcctgaag gagggcatcg ctaagaaggc tgccaactcc   1140
atcctggtta aggtgaacca gatcggtacc ctcaccgaga ccttcgacgc tgtcgacatg   1200
```

-continued

```
gctcaccgcg caggctacac ctccatgatg tcccaccgtt ccggtgagac cgaggacacc      1260
accattgctg acctcgcagt tgcactcaac tgtggccaga tcaagactgg tgctccagca      1320
cgttccgacc gtgtcgcaaa gtacaaccag cttctccgca tcgagcagct gcttggcgac      1380
gccggcgtct acgcaggtcg cagcgcattc ccacgctttc agggctaaat aaaagcgctt      1440
ttcgacgccc ggtaacctca aggttgccgg gcgtcgttgc cttactactg ttactggtgt      1500
gactatgatc gaggattatg caaagcaga agaaaactca taaggcctt gttcctgtct       1560 caagcaggga acgtgctt                                                    1578
```

<210> SEQ ID NO 4
<211> LENGTH: 425
<212> TYPE: PRT
<213> ORGANISM: Corynebacterium glutamicum

<400> SEQUENCE: 4

```
Val Ala Glu Ile Met His Val Phe Ala Arg Glu Ile Leu Asp Ser Arg
1               5                   10                  15

Gly Asn Pro Thr Val Glu Ala Glu Val Phe Leu Asp Asp Gly Ser His
            20                  25                  30

Gly Val Ala Gly Val Pro Ser Gly Ala Ser Thr Gly Val His Glu Ala
        35                  40                  45

His Glu Leu Arg Asp Gly Gly Asp Arg Tyr Leu Gly Lys Gly Val Leu
    50                  55                  60

Lys Ala Val Glu Asn Val Asn Glu Glu Ile Gly Asp Glu Leu Ala Gly
65                  70                  75                  80

Leu Glu Ala Asp Asp Gln Arg Leu Ile Asp Glu Ala Met Ile Lys Leu
                85                  90                  95

Asp Gly Thr Ala Asn Lys Ser Arg Leu Gly Ala Asn Ala Ile Leu Gly
            100                 105                 110

Val Ser Met Ala Val Ala Lys Ala Ala Ala Asp Ser Ala Gly Leu Pro
        115                 120                 125

Leu Phe Arg Tyr Ile Gly Gly Pro Asn Ala His Val Leu Pro Val Pro
    130                 135                 140

Met Met Asn Ile Ile Asn Gly Gly Ala His Ala Asp Ser Gly Val Asp
145                 150                 155                 160

Val Gln Glu Phe Met Ile Ala Pro Ile Gly Ala Glu Thr Phe Ser Glu
                165                 170                 175

Ala Leu Arg Asn Gly Ala Glu Val Tyr His Ala Leu Lys Ser Val Ile
            180                 185                 190

Lys Glu Lys Gly Leu Ser Thr Gly Leu Gly Asp Glu Gly Gly Phe Ala
        195                 200                 205

Pro Ser Val Gly Ser Thr Arg Glu Ala Leu Asp Leu Ile Val Lys Ala
    210                 215                 220

Ile Glu Lys Ala Gly Phe Thr Pro Gly Lys Asp Ile Ala Leu Ala Leu
225                 230                 235                 240

Asp Val Ala Ser Ser Glu Phe Phe Lys Asp Gly Thr Tyr His Phe Glu
                245                 250                 255

Gly Gly Gln His Ser Ala Ala Glu Met Ala Asn Val Tyr Ala Glu Leu
            260                 265                 270

Val Asp Ala Tyr Pro Ile Val Ser Ile Glu Asp Pro Leu Gln Glu Asp
        275                 280                 285

Asp Trp Glu Gly Tyr Thr Asn Leu Thr Ala Thr Ile Gly Asp Lys Val
    290                 295                 300
```

-continued

```
Gln Ile Val Gly Asp Asp Phe Phe Val Thr Asn Pro Glu Arg Leu Lys
305                 310                 315                 320

Glu Gly Ile Ala Lys Lys Ala Ala Asn Ser Ile Leu Val Lys Val Asn
                325                 330                 335

Gln Ile Gly Thr Leu Thr Glu Thr Phe Asp Ala Val Asp Met Ala His
                340                 345                 350

Arg Ala Gly Tyr Thr Ser Met Met Ser His Arg Ser Gly Glu Thr Glu
                355                 360                 365

Asp Thr Thr Ile Ala Asp Leu Ala Val Ala Leu Asn Cys Gly Gln Ile
            370                 375                 380

Lys Thr Gly Ala Pro Ala Arg Ser Asp Arg Val Ala Lys Tyr Asn Gln
385                 390                 395                 400

Leu Leu Arg Ile Glu Gln Leu Leu Gly Asp Ala Gly Val Tyr Ala Gly
                405                 410                 415

Arg Ser Ala Phe Pro Arg Phe Gln Gly
                420                 425

<210> SEQ ID NO 5
<211> LENGTH: 20
<212> TYPE: DNA
<213> ORGANISM: PCR primer

<400> SEQUENCE: 5
ttggcatagg aggccacagt                                              20

<210> SEQ ID NO 6
<211> LENGTH: 20
<212> TYPE: DNA
<213> ORGANISM: PCR primer

<400> SEQUENCE: 6
atttagccct gaaagcgtgg                                              20
```